US010398099B2

(12) United States Patent
Cope et al.

(10) Patent No.: US 10,398,099 B2
(45) Date of Patent: *Sep. 3, 2019

(54) GRAIN PRODUCTION

(71) Applicant: Accelerated Ag Technologies, LLC, Urbandale, IA (US)

(72) Inventors: Jason Cope, Ankeny, IA (US); Todd Krone, Johnston, IA (US); George Singletary, Ankeny, IA (US)

(73) Assignee: Accelerated Ag Technologies, LLC, Ankeny, IA (US)

( * ) Notice: Subject to any disclaimer, the term of this patent is extended or adjusted under 35 U.S.C. 154(b) by 91 days.

This patent is subject to a terminal disclaimer.

(21) Appl. No.: 15/192,519

(22) Filed: Jun. 24, 2016

(65) Prior Publication Data
US 2016/0374280 A1   Dec. 29, 2016

Related U.S. Application Data

(60) Provisional application No. 62/269,514, filed on Dec. 18, 2015, provisional application No. 62/269,531, filed on Dec. 18, 2015, provisional application No. 62/269,496, filed on Dec. 18, 2015, provisional application No. 62/184,596, filed on Jun. 25, 2015.

(51) Int. Cl.
*A01H 1/02* (2006.01)
*A01H 6/54* (2018.01)
*A01H 6/46* (2018.01)

(52) U.S. Cl.
CPC ............. *A01H 1/02* (2013.01); *A01H 6/4684* (2018.05); *A01H 6/542* (2018.05)

(58) Field of Classification Search
None
See application file for complete search history.

(56) References Cited

U.S. PATENT DOCUMENTS

| | | | |
|---|---|---|---|
| 4,087,937 | A | 5/1978 | Meador |
| 5,596,838 | A | 1/1997 | Greaves et al. |
| 5,689,914 | A | 11/1997 | Greaves et al. |
| 5,694,700 | A | 12/1997 | Grooves et al. |
| 6,141,904 | A | 11/2000 | Greaves et al. |
| 6,146,884 | A | 11/2000 | Coonrod et al. |
| 6,865,556 | B2 | 3/2005 | Penner et al. |
| 8,158,850 | B2 | 4/2012 | Feng et al. |
| 8,356,464 | B2 | 1/2013 | Lafargue et al. |
| 8,618,358 | B2 | 12/2013 | Feng et al. |
| 8,943,745 | B2 | 2/2015 | Sexton et al. |
| 9,227,230 | B2 | 1/2016 | Bensley-Bromilow et al. |
| 9,433,161 | B2 | 9/2016 | Cope et al. |
| 2013/0118066 | A1 | 5/2013 | Cope et al. |
| 2013/0118067 | A1 | 5/2013 | Cope et al. |
| 2013/0167496 | A1 | 7/2013 | Bensley-Bromilow et al. |
| 2014/0115730 | A1 | 4/2014 | Cope |
| 2014/0223812 | A1 | 8/2014 | Cope et al. |

FOREIGN PATENT DOCUMENTS

| | | | |
|---|---|---|---|
| CA | 966734 | 4/1975 | |
| CN | 104145947 | 11/2014 | |
| CN | 104957032 | * 10/2015 | |
| CN | 205926293 | * 2/2017 | |
| JP | H11192033 | 7/1999 | |
| JP | 200904703 | 2/2009 | |
| JP | 2009040703 | 2/2009 | |
| SU | 1061770 | 12/1983 | |
| SU | 1606037 | * 11/1990 | ............... A01H 1/02 |
| WO | WO-2012125593 A2 | * 9/2012 | ............... A01H 1/02 |
| WO | WO213/070846 | 5/2013 | |
| WO | WO2014147005 | 9/2014 | |
| WO | WO2014209903 | * 12/2014 | |
| WO | WO-2016085355 A1 | * 6/2016 | ............. A01H 1/025 |
| WO | WO-2018129302 A1 | * 7/2018 | ............. A01H 1/025 |

OTHER PUBLICATIONS

Ortiz-Perez et al. Field Crops Research 101: 259-268 (2007).*
Graybosch et al. American Journal of Botany 75(1): 144-156 (1988).*
Office Action dated Oct. 12, 2018 from U.S. Appl. No. 15/192,485.*
Connor, Kristina F. (1993) "Pollen-Handling protocol and hydration/dehydration charactreristics of pollen for application to long-term storage", Euphytica 68: 77-84.*
Sanford et al. (1977) American Potato Journal 54: 573-574.*
Bhargava et al. (1991) American Potato Journal 68: 581-582.*
EPC Communication pursuant to Rules 161(1) and 162 re European Patent App. No. 17 718 712.7 dated Nov. 28, 2018.*
International Search Report and Written Opinion of the International Search Authority regarding PCT/US2016/039355 filed on Jun. 24, 2016, (dated Aug. 10, 2016).
R T Weiland: Cross-Pollination Effects on Maize (*Zea mays* L.) hybrid yields, CAN, J. Plant Sci, vol. 72, No. 1, Jan. 1, 1992, pp. 27-33.

(Continued)

*Primary Examiner* — David T Fox
(74) *Attorney, Agent, or Firm* — Brick Gentry PC; Brian J. Laurenzo; Jessica L. Susie

(57) ABSTRACT

This invention describes a new method to increase grain yields in any crop plant by modifying pollination to effect an increase in grain yield, a change in grain content or characteristics, a decrease in contamination, or a combination of these attributes. The process involves the intentional delivery of pollen of the male plant at will, as available either in a preserved pollen bank, or real-time collection from male plants as they become available, in a growth chamber for example. Desired pollen is delivered to fertile females. The delivered pollen$^M$ is in such amounts and fortuitously timed that it preferentially pollinates the females and optionally, avoids or enhances self-pollination or pollination from neighboring plants. The intentional delivery of genetically different pollen will result in increased heterosis and accompanying grain yield increases resulting from increased grain size and the potential to influence grain content and constituents. The invention also permits real-time agronomic decision making in order to maximize grain yield by overcoming biotic and abiotic challenges in the growing season which may or may not have been anticipated. The intentional delivery of self- or sib-pollen results in a decrease in contamination from undesirable outcrossing.

25 Claims, 3 Drawing Sheets

(56) References Cited

OTHER PUBLICATIONS

Cherng-Liang Tsai Et Al: Effects of cross-pollination on dry matter accumulation, nutrient partitioning and grain yield of maize hybrids grown under different levels of N fertility, Journal of the Science of Food and Agriculture, vol. 57, No. 2, Jan. 1, 1991, pp. 163-174.
J M Shete et al: Study of Heterosis in Top Cross Derivatives of Maize (Zea Mays L.), Agric. Sci. Digest, vol. 31, No. 1, Mar. 1, 2011, pp. 1-7.
Wang R F et al: Leaf photosynthesis is enhanced in normal oil maize pollinated by high oil maize hybrids, Industrial Crops and Products, Elsevier, NL, vol. 29, No. 1 , Jan. 1, 2009. pp. 182-188.
Uribelarrea et al: Enhanced kernel set promoted by synchronous pollination determines a tradeoff between kernel number and kernel weight in temperate maize hybrids, Field Crops Research, Elsevier, Amsterdam, NL, vol. 105, No. 3, Nov. 19, 2007, pp. 172-181.
Carcova Jorgelina et al: Synchronous pollination within and between ears improves kernel set in maize, Crop Science, vol. 40, No. 4, Jul. 2000, pp. 1056-1061.
Barnabas, B. and Rajki, E. (1976). Storage of Maize (Zea mays L.) Pollen at—196° C. in Liquid Nitrogen. Euphytica 25:747-752.
Barnabas, B. (1981) Fertility of deep-frozen maize (Zea mays L.) pollen. Ann. Bot. 48:861-864. + Rajki , E.
Barnabas B.(1985). Effect of water loss on germination ability of maize (Zea mays L.) pollen. Ann. Bot. 55:201-204.
Barnabas, B; Kovacs, G.; Abranyi, A.; and Pfahler, P. (1988). Effects of Pollen Storage by Drying and Deep-Freezing on the Expression of Different Agronomic Traits in Maize (Zea mays L.). Kluwer Academic Publishers, Dordrecht-Printed in the Netherlands. Euphytica 39(3):221-225.
Barnabas, B (1994). Preservation of Maize Pollen Biotechnology in Agriculture and Forestry, vol. 25 Maize (ed. By Y. P. S. Bajaj) Springer-Verlag Berlin Heidelberg, (pp. 607-618).
Barnabas, B., and G. Kovacs. (1997). Storage of Pollen. Ch. 14, In: K.R. Shivanna and V. K. Sawhney (eds). Pollen Biotechnology for Crop Production and Improvement. Cambridge University Press, (pp. 293-314).
Basra, A. (1999). Heterosis and Hybrid Seed Production in Agronomic Crops, 81-84.
Collins, T. C.; Lertmongkol, V.; Jones, J. P. (1973). Pollen Storage of Certain Agronomic Species in Liquid Air, Crop Science, 13:493-494.
Connor, Kristina and Towill, Leigh. (1993). Pollen-Handling Protocol and Hydration/Dehydration Characteristics of Pollen for Application to Long-Term Storage, KluwerAcademics Publisher 4, (Euphytica 68: 77-84).
Clegg. J.S.; Seitz, P.; Seitz, W.; Hazlewood, C.F. (1982). Cellular responses to extreme water loss: the water-replacement hypothesis. Cryobiology 19:306-316.
Crevecoeur, M.; Deltour. R.; Bronchart, R. (1982). Quantitative freeze-fracture study of plasmalemma and nuclear-envelope of Zea mays root cells during early germination. J. Ultrastruct. Res. 80:1-11.
Das, S.; Singhal, G.S. (1985). Role of interfacial structured water in membrane: osmotic properties of L-α-Egg lecithin liposomes. J. Membr. Biol. 86:221-227.
Notification Concerning Transmittal of International Preliminary Report on Patentability and International Preliminary Report on Patentability from PCT/US2016/039339, (Dec. 26, 2017).
Notification Concerning Transmittal of International Preliminary Report on Patentability and International Preliminary Report on Patentability from PCT/US2016/039355, (Dec. 26, 2017).
Dickinson, H.G.; Elleman, C.J. (1985). Structural changes in the pollen grain of Brassica oleracea during dehydration in the anther and development on the stigma as revealed by anhydrous fixation techniques. Micron Micros. Acta 16:255-270.
Elleman, C.J.; Dickinson, H.G. (1986). Pollen stigma interactions in Brassica. IV. Structural reorganisation in the pollen grains during hydration. J. Cell Sci. 80:141-157.
Ganeshan, S., et al. (2008). Cryopreservation of Pollen. Ch. 17, In: B.M. Reed (ed), Plant Crypreservation: A Practical Guide. Springer, (pp. 443-464).
Heslop-Harrison, J. (1979). An interpretation of the hydrodynamics of pollen. Amer. J. Bot. 66: 737-743.
Heslop-Harrison, J.; Heslop-Harrison, Y. (1985). Germination of stress tolerant Eucalyptus pollen. J. Cell Sci. 73:135-157.
Hoekstra, F.A., and J. Bruinsma. (1975). Respiration and vitality of binucleate and trinucleate pollen. Physiol. Plant. 34: 221-225.
Kaku, S.; Iwayainove, M.; Gusta, L.V. (1984). Relationship of nuclear magnetic resonance relaxation time to water content and cold hardiness in flower buds of evergreen azalea. Plant Cell Physiol. 25:75-882.
Khatum, S., and T.J. Flowers. (1995). The estimation of pollen viability in rice. J. Exp. Bot. 46:151-154.
King, J.R.(1965). The storage of pollen-particularly by the freeze drying method. Bull. Torrey Bot. Soc. 92: 270-287.
Swift, J.G.; Buttrose, M.S. (1972). Freeze-etch studies of protein bodies in wheat scutellum. J. Ultrastruct. Res. 40:378-390.
Virmani, S.S. and M. Llyas Ahmed. (2001). Environment-sensitive genic male sterility (EGMS) in crops. Adv. Agronomy 72: 139-195. DOI: 10.1016/S0065-2113(01)72013-5.
Walden, D. B. (1967). Male Gametophyte of Zea mays L. Crop Science 7:441-443.
Wang, Z: Ge, Y.; Scott. M and Spangenberg, G. (2004). Viability and longevity of pollen from transgenic and non-transgenic tall Fescue (Festuca arundinacea) (Poaceae) Plants. American Journal of Botany 91(4): 523-530.
Webb, M.A.; Arnott, H.J. (1982). Cell wall conformation in dry seeds in relation to the preservation of structural integrity during desiccation. Am. J. Bot. 69:1657-1668.
Pareddy et al. (1989). Production of normal, germinable and viable pollen from in vitro-cultrued maize tassels. Theor Appl. Genet. 77:521-526.
Aylor, Donald E. (2004). Survival of maize (Zea mays) pollen exposed in the atmosphere. Agricultural and Forest Meteorology 123 (2004) 125-133.
Buitink et al. (2000). The effects of moisture and temperature on the ageing kinetics of pollen: interpretation based on cytoplasmic mobility. Plant Cell and Environment (2000) 23, 967-974.
Everett, H.L. (? 1954s?) Studies on Corn Pollen. Thirteenth Hybrid Corn Industry Research Conference, (pp. 47-53).
Kerhoas C. et al. (1987). A multidisciplinary approach to the study of the plasma membrane of Zea mays pollen during controlled dehydration. 10. Planta 171: 1-10.
Nath, J. et al. (1975) Effect of Freezing and Freeze-Drying on the Viability and Storage of Lilium longiflorum L. and Zea mays L. Pollen. Cryobiology 12, 81-88.
Nepi, M. et al. (2001). Pollen hydration status at dispersal: cytophysiological features and strategies. Protoplasma (2001) 216: 171-180.
Urs Weingartner, Olivier Kaeser, Muhua Long, and Peter Stamp: Combining Cytoplasmic Male Sterility and Zenia Increases Grain Yield of Maize Hybrids, Crop Science, pp. 1848-1856 (2002).
International Search Report and Written Opinion of the International Searching Authority regarding PCT/US2016/039339 filed on Jun. 24, 2016 (dated Sep. 21, 2016).
Synchronous Pollination within and between Ears Improves Kernel Set in Maize, Crop Science, vol. 40, No. 4, Jul. 2000, pp. 1056-1061.
U.S. Appl. No. 15/192,485 Covering Seed Production dated Jan. 22, 2018.
Koga, Y., et al. (1971). Studies on the longevity of pollen grains of rice, Oriza sativa L. 1. Morphological change of pollen grains after shedding. Cytologia 36: 104-110.
Mouradian, R.; Womersley, C.; Crowe, L.M.: Crowe, J.H. (1985). Degradation of functional integrity during long-term storage of a freeze-dried biological membrane. Cryobiology 22:119-127.

(56) References Cited

OTHER PUBLICATIONS

Pfahler, P. L.; Linskens, H. F. (1972). In vitro germination and pollen tube growth of maize (*Zea mays* L.) pollen Theoretical and Applied Genetics, 42:136-140.

Platt-Aloia, K.A.; Lord, E.M.; de Mason, D.A.; Thompon, W.W. (1986). Freeze fracture observations on membranes of dry and hydrated pollen from Colomia, Phoenix and Zea. Planta 168:291-298.

Platt-Aloia, K.A.; Thomson, W.W. (1985). Freeze-fracture evidence of gel-phase lipid in membranes of senescing cowpea cotyledons. Planta 163:360-369.

Priestley, D.A.; De Kruijff; B. (1982). Phospholipid motional characteristics in a dry biological system. A 31P nuclear magnetic resonance study of hydrating Typha latifolia pollen. Plant Physiol. 70:1075-1078.

Priestley, D.A.; Werner, B.G.; Leopold, A.C.; McBride, M.B. (1985). Organic free radical levels in seeds and pollen: the effects of hydration and aging. Physiol. Plant. 64:88-94.

Senaratna, T.; McKersie, B.D.; Stinson. R.H. (1985). Simulation of dehydration injury to membranes from soybean axes by free radicals. Plant Physiol. 77:472-474.

Song, Z.P., et al. (2001). A study of pollen viability and longevity in Oryza rufipogon, O. sativa, and their hybrids. p. 31-32. IRRI Pub. 26.2.

Southworth, D.; Branton, D. (1971). Freeze-etched pollen walls of Artemisia pycnocephala and Lolium humboldtii. J. Cell Sci. 9:193-207.

International Search Report and Written Opinion of the International Searching Authority from PCT/US2017/027381, (Jul. 11, 2017).

Office Action dated Apr. 30, 2018 from U.S. Appl. No. 15/486,737 Covering Pollen Field Conditioning and Preservation Method.

Almeida et al (Brazilian Journal of Botany (2011), Conservacao e germinacao in vitro de polen de milho, vol. 34 (4), pp. 493-497.

Volk, Gayle (2011) Collecting Pollen for Genetic Resources Conservation. Ch. 25, pp. 1-10.

Communication pursuant to Article 94(3) EPC regarding European Patent Application No. 16 739 302.4 dated Feb. 12, 2019 Covering Seed Production.

Communication pursuant to Article 94(3) EPC regarding European Patent Application No. 16 738 296.9 dated Feb. 18, 2019 Covering Grain Production.

Office Action dated Apr. 12, 2019 from U.S. Appl. No. 15/486,737 Covering Pollen Field Conditioning and Preservation Methos.

Ishikawa, M. Kitashima, T., Hemachandra, P.V., Yamaguchi, E. and Toyomasu, T. (2005), Seed Sci. & Technol., 33, 741-752 Constant relative humidity chambers using phosphoric acid for controlled desiccation of small recalcitrant.

* cited by examiner

GRAIN PRODUCTION

CROSS REFERENCE TO RELATED APPLICATIONS

This application claims priority from U.S. Provisional Application Ser. No. 62/184,596 filed Jun. 25, 2015 and entitled SEED PRODUCTION, and from U.S. Provisional Application Ser. No. 62/269,496 filed Dec. 18, 2015 and entitled SEED PRODUCTION, and from U.S. Provisional Application Ser. No. 62/269,531 filed Dec. 18, 2015 and entitled GRAIN PRODUCTION, and from U.S. Provisional Application Ser. No. 62/269,514 filed Dec. 18, 2015 and entitled GRAIN PRODUCTION. The contents of U.S. Provisional Application Ser. Nos. 62/184,596; 62/269,496; 62/269,531; and 62/269,514 are hereby incorporated in their entireties by reference.

FIELD OF THE INVENTION

This invention relates generally to novel methods of grain production, specifically intended to increase grain yields. More specifically, this invention relates to on-demand pollination technology applicable to grain-bearing plants which is not dependent on active pollen shed, neighboring plants, or seed mixes.

BACKGROUND

The current invention has application to the field of grain production and plant pollination practices, including, but not limited to, economically significant grain crops such as maize (also called corn), soybeans, wheat, rice, sunflower, canola, sorghum, barley, and pearl millet. The term "grain production" as used in this disclosure is intended to mean commercial-scale grain production, using a minimum field size of 0.8 hectares (2 acres) of land for the production of said grain. A conventionally grown grain field is typically predominantly F1 plants that share genes in common from 2 inbred parents (although conventional grain will also have a small percentage of contaminant seed (not F1) in a standard bag of seed.). In other situations, the "top-cross" method is used for grain production. In contrast to the conventional field of F1 plants, top-cross grain uses a field that is a blend of a male sterile hybrid (~93%) and a male fertile high oil pollinator germplasm (7%). Commercial grain production often relies upon field production of hybrid plants. Hybrid plants are the result of fertilization occurring from a male pollen source of one genetic background being crossed to the female reproductive organs of a plant with a different genetic background. Hybridity among crop plants generally gives a yield advantage in commercial production. Currently, maize, rice, sorghum, sunflower, and canola are the primary crops which take advantage of hybrid seed. Other grains are less commonly grown as hybrids, as is the case with soybean, wheat, barley, pearl millet and others.

For crops in which grain production is commonplace, current methods of producing grain vary slightly by species, but typically involve planting fields of the same seed variety to produce plants whose mature seeds will result in the desired grain. The plants in such fields are typically self-pollinated or pollinated by neighboring plants in the field. There may be some cross pollination from nearby fields of similar species.

For the purposes of this disclosure and its applicability to grain production, the term "self-pollen," which is a single plant's own pollen, includes "sib-pollen," which is pollen from sibling plants who share the same genetics. Likewise, the term "self-pollination" includes "sib-pollination." which is pollination occurring with pollen from a sibling plant, and which has the same effect in the resulting grain as self-pollination. In a hybrid grain production field, all self-pollination and sib-pollination is effectively self-pollination in terms of the effect on the grain, which is a yield decrease (in comparison to outcrossing) and purity increase in the case of food corn. "Cross pollination," for the purposes of this disclosure, refers to genetic exchange between inbreds or hybrids in adjacent and surrounding fields, not from plants within the same field. Thus, cross pollination is the introduction of pollen that is derived or sourced from separate locations that is genetically distinct from the pollen which will be shed from the plants within the grain production field.

The advantage of using hybrid seed for grain production is that hybrids are known to exhibit heterosis, which is expressed as hybrid vigour, meaning a stronger and more resilient plant. Heterosis also results in higher grain yields. This effect is sometimes referred to as xenia. (Stamp et al. (2002) *Crop Sci.* 42:1848-1856; Stamp et al. (2002) *Maydica* 47:127-134). Heterosis also occurs when an existing hybrid plant (created from 2 different parent plants) is fertilized with pollen from yet another plant, providing a subsequent boost in yield. Hybrid grain crops substantially out yield non-hybrid cultivars and also exhibit better response to fertilizers. However, conditions during the growing season vary from year to year and pressures caused by environmental challenges, disease outbreaks and insect infestations can significantly impact grain yield.

Theoretically, cross pollinating hybrids can provide a yield benefit by avoiding the in-breeding depression associated with self- or sib-pollination, or by creating new gene combinations that generate a heterotic response within the kernels. This response has been termed the 'xenia effect.' "Xenia can be defined as the effect of the pollen genes on the development of the fruit or the seeds." (Bulant et al. ((2000) *Crop Sci.* 40: 182-188)

Numerous studies have shown the influence of the pollen source on the development of the kernel. Among the earliest demonstrations (Kiesselbach, T. A. (1926) *Neb. Agric. Exp. Stn. Bull.* 33:1-69; Kiesselbach. T. A. & W. H. Leonard (1932) *J. Am. Sc. Agron.* 24:517-523), Kiesselbach reported that relative to self-fertilization, cross fertilization increased kernel weights on average by 10.1% (11.8% for embryos, 10.4% for endosperm, and 3.2% for pericarp). Tsai and Tsai (Tsai, C. L. & C. Y. Tsai (1990) *Crop Sci.* 30: 804-808) showed an increase in grain yield of about 30% and in increase in kernel protein content of about 44% in an early hybrid when it was pollinated by a late hybrid. Using maize inbred lines with normal endosperm, Bulant et al. ((2000) *Crop Sci.* 40: 182-188) reported a relative advantage in weight of cross-fertilized to self-fertilized kernels as great as 13%. Breeding studies at South Dakota State University confirm that cross pollination of specific hybrids can increase kernel size and protein content, and that cross pollination between hybrids of similar maturity accounts for 40 to 60% of kernels formed in mixed stands (Wicks III, Z., (1994) *Proc. Annual Corn and Sorghum Res. Conf.* 4.

The development of the kernels can be altered by cross pollination (Tsai, C. L. & C. Y. Tsai (1990) *Crop Sci.* 30: 804-808; Poneliet, C. G. and D. B. Egli, (1983) *Crop Sci.* 23:872-875). Poneliet and Egli (1983) showed that the duration of the effective filling period from cross-fertilization often was greater than that from self-fertilization. Pollen source also affects endosperm development in terms of protein content, amino acid profile, and translucency. (Pixley. K. V. and M. S. Bjarnason (1994) *Crop Sci.* 34:404-408: Bulant et al. (2000) *Crop Sci.* 40: 182-188). At 14 DAP, the advantage of cross-fertilization on average was 28.8% for starch content, 24.8% for ADP-glucose-pyrophosphorylase (EC 2.7.7.27) activity, and 24.1% for neutral invertase (EC 3.2.1.26) activity (Bulant et al. (2000) *Crop Sci.* 40: 182-188). Tsai et al. ((1991) *J. Sci. Food Agric.* 57: 163-174) modified P3732 endosperm through cross-pollination, which significantly increased kernel weight, kernel protein content and grain yield across a range of fertilizer N treatments. The additional nutrients translocated into developing kernels of P3732 cross-pollinated plants were mainly derived from increases in duration of dry matter production and N uptake by vegetative tissues (Tsai et al. (1991) *J. Sci Food Agric.* 57: 163-174). These well-established impacts on kernel composition are the basis for the top-cross method of producing high oil corn. The top-cross system for high oil corn grain production was a method used in the 1990s and early 2000s in which high oil was induced by planting a blend of a male sterile hybrid (~93%) and a male fertile high oil pollinator germplasm (7%). The result was an increase in oil from about 3-4% for normal commodity grain, to about 6% for the high oil top-cross grain. The high oil grain brought a premium price per bushel at the grain elevator. (Thomison. P. R. et al. (2002) *Agron. J.* 94: 290-299.)

The extent of the xenia effect varies with the male and female genotype. The greater the genetic difference between the male pollen source and female, the greater the expected response to cross-pollination. (Leng, E. R., (1949) *Agron. J.* 41:555-558; Bulant, C. and A. Gallais, (1998) *Crop Sci.* 38: 1517-1525). The cross fertilization advantage was less for single-cross hybrids than for their inbred parents, and the advantage varies with the male. For crosses between inbreds, the advantage of cross fertilization was 13.8 and 14.5%, but only 2.5% for crosses made with their hybrid (Bulant. C. and A. Gallais, (1998) *Crop Sci.* 38: 1517-1525). Both pollen and maternal effects impact the response to cross pollination (Seka, D and I. Z. Cross (1995) *Crop Sci.* 35: 80-85; Seka. D. et al. (1995) *Crop Sci.* 35: 74-79).

Results of cross pollinations between hybrids observed by Bulant and Gallais (Bulant, C. and A. Gallais, (1998) *Crop Sci.* 38: 1517-1525) illustrate that cross fertilization can increase the sink strength of the whole ear and that the kernel mass benefit can be observed under unfavorable conditions. The positive xenia effects have been interpreted in terms of source-sink relationships. If the resources are limiting, the increase in sink strength leads to a greater average kernel weight with mixed fertilization than with pure self-fertilization. There was no relationship between the cross-fertilization advantage and the average seed weight of the self-fertilized female or male pollen source. Cross-fertilization advantage was beneficial for small kernels as well as for large kernels (Bulant, C. and A. Gallais, (1998) *Crop Sci.* 38: 1517-1525).

Pollination success is critical to grain yield. Grain yield is measured as the weight of grain per area of land measured at a given moisture content (for example, 15.5% moisture for corn). Low pollination rates result in poor grain yield. For this reason, grain producers typically rely upon self-pollination and pollination by neighboring plants in the field since they know that the pollination will occur during the correct window of time because the female components of the plant will be ready to receive the pollen. Unfortunately, self-pollination will not necessarily maximize grain yield and it is unable to account for changing conditions and stresses that may affect the plant during the growing season.

Accordingly, there is a need in the industry for an invention which allows for the improvement of grain yield, grain content, grain purity, grain characteristics, decreased contamination, or a combination of these attributes. The instant invention provides a method for the improvement of grain yields by intentionally cross-pollinating the plants producing the grain. In addition, the instant invention provides a method for the increase of grain size and the modification of grain constituents by means of specific cross-pollination with pollen from a different genetic background, the method for which also allows for real-time production decisions to address conditions at the time of pollination or to address production challenges. This method can also reduce undesirable contamination in the grain harvested from the field. The instant invention also provides a method of maximizing synchronous pollination with self- or sib-pollen, which provides for the reduction of contamination caused by undesirable cross-pollination, which is particularly applicable to the organic farming industry. These two methods can also be combined to both increase yield and modify grain size and constituents in the same grain field, while also reducing contamination.

The invention described herein would enable a 5% grain yield increase in corn (a conservative estimate), the annual value of this invention with 33% adoption, mostly on higher productivity land, would be $1.1 billion to the entire value chain in the U.S. alone. This is based on 2015 US corn production of 345 metric tons (U.S. Corn Growers Association (2016) World of Corn [online, retrieved on 2016 Jun. 13], Retrieved from the internet) and a corn commodity price of $185.04 per metric ton (Jun. 13, 2016 corn price [online, retrieved on 2016 Jun. 13] Retrieved from the internet) (Calculation: $185.04/MT×345 MM MT×5% yield increase×33% adoption). Likewise, the invention described herein could enable a 5% grain yield increase in rice, which would have an annual value, with 10% adoption, mostly by larger farmers on highly productive land, of $1.5 billion globally. This is based on 2013 global rice production of 746 MM metric tons (GeoHive (2016) [online] World: Rice Production in Metric Tonnes, retrieved on 2016 Jun. 20. Retrieved from the internet) and a rice commodity price of $408.91 per metric ton (May 2016 rough rice commodity price [online], retrieved from the internet on 2016 Jun. 23. Retrieved from the internet) (Calculation: $408.91/MT×746 MM MT×5% yield increase×10% adoption).

SUMMARY OF THE INVENTION

Figure 1:
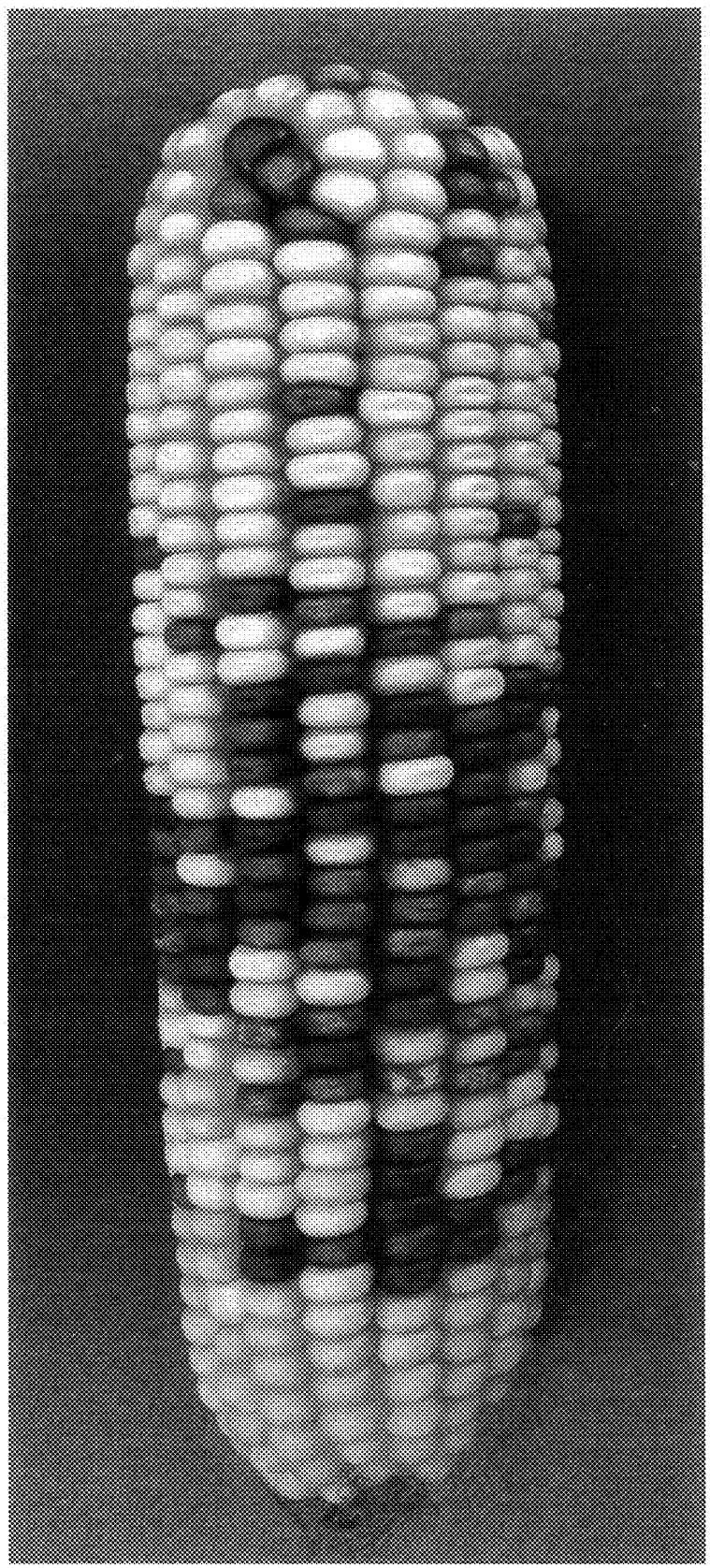
FIG. 1: This figure is a photograph of an ear of corn harvested from hybrid H2 and pollinated with pollen from pollen donor P2 as described in Example 2. The photograph is shown in black and white. The color version of the photograph shows the light colored kernels in yellow and the darker colored kernels in purple. This ear shows the successful cross-pollinations that occurred throughout the ear. The self pollinations are the light kernels and the cross-pollinations are the dark kernels. This ear was useful for determining yield differences between the two pollination types.

Provided is a method of improving commercial grain production of any plant species by intentionally cross-pollinating grain plants with pollen from a different genetic background. This method provides a yield increase as a result of heterosis, or the xenia effect. This method has the additional benefit of providing for modification of grain characteristics, including grain content and grain constituents.

Also provided is a method of enhancing levels of self- and/or sib-pollination in commercial grain production, the method including the intentional application of designated male pollen (with the same genetic background as the designated female plant) to a designated female plant on one or more occasions. At the time of the intentional application, the designated female plant is in a state when the female components are ready to receive pollen. The male components of the designated female plant may or may not be releasing pollen at the time of the intentional application of designated male pollen. In the event that the male components are releasing pollen, some female components will receive the intentionally applied designated male pollen while other components may receive self-pollen or sib-pollen from neighboring plants, resulting in an overall increase in successful pollination events, and thereby reducing contamination caused by undesirable outcrossings.

One embodiment of the invention is a method of increasing grain size and modifying grain characteristics, including grain content and constituents, by means of specific cross-pollination. For example, the oil, protein or starch content of the grain may be modified, and the specific oil, protein or starch constituents of the grain may also be modified. This method provides for the use of real-time production decisions to address specific conditions at the time of pollination, and allows the grower to address specific production challenges in the field. At the time of the intentional application, the designated female plant is in a state when the female components are ready to receive pollen. The male components of the designated female plant may or may not be releasing pollen at the time of the intentional application of designated male pollen. In the event that the male components are releasing pollen, some female components will receive the intentionally applied designated male pollen while other components may receive self-pollen or sib-pollen from neighboring plants. In the event that the male components are not releasing pollen, the majority of the female components will receive the intentionally applied designated male pollen from a different genetic background, resulting in heterosis, or the xenia effect, and a concurrent increase in the size of grains or kernels, as well as intentional changes in grain content or constituents.

Both these methods can also help to reduce contamination in the grain caused by undesirable pollination events. The methods may also be combined in order to achieve both a grain yield increase and an increase in grain size, along with the modification of grain characteristics.

The methods are applicable to a wide range of plants including, but not limited to, corn, soybean, wheat, rice, sunflower, canola, sorghum, cotton, barley, and pearl millet. The application of the designated male pollen may be conducted by automated means, mechanical means, positive pressure means, negative pressure means, manual means, semi-automated means, or combinations thereof. Moreover, the designated male pollen source may be from previously preserved or freshly harvested pollen from male source material. The pollen may have been harvested from one or more of a field, a growth chamber, a greenhouse, a glasshouse, a shade house, a hoop house, a vertical farming facility or a hydroponic facility. Preserved pollen may have been preserved by any means that permits the pollen to retain viability, including but not limited to various forms of cooling or freezing including, but not limited to, chilling, cryopreservation, freeze drying, or storage in liquid nitrogen. Furthermore, the pollen, whether fresh or preserved, may have been collected from a source with altered circadian rhythm or a source with normal circadian flowering, but wherein said male components of said designated female parent plants are delayed, or allowed to shed with no delay. The pollen, whether fresh or preserved, may have been collected from one or more sources and may have been combined with pollen from other sources before application.

Further provided is a method of improving crop productivity. The method includes intentionally applying specifically selected pollen from a genetically unrelated source and allows the opportunity for making real-time, agronomic-specific decisions in selecting the unrelated pollen sources. This method allows the maximization of seed characteristics for any given environmental condition or market needs for any given plant of interest. For example, in one embodiment, the specifically selected pollen is obtained from sources optimal for application based on environmental conditions, including abiotic and biotic conditions. In another embodiment, the specifically selected pollen is obtained from a source optimal for application based on plant performance data (such as data obtained from yield trials, for example), or commodity and market price information. In yet another embodiment, the specifically selected pollen influences the characteristics of the grain harvested from the female plant, impacting characteristics such as grain content and constituents, which include, but are not limited to, grain oil content and composition, grain starch content and composition, and grain protein content and composition.

In an embodiment of this invention, the designated female plants may be either male sterile or male fertile, and the pollen source may be applied prior to exposure from a designated female plant pollen, including self-pollen or it may be applied concurrently while the plant is receptive to self-pollen and/or sib-pollen. Moreover, the method may include male-specific pollen sources which are optimal for application of pollen based on environmental conditions or on market trends which would make seeds with a specific composition (i.e., starch, oil, drought resistance, flood tolerance, etc.), more valuable. Furthermore, the pollen may be selected from a single source or a combination of sources in order to enable a combination of traits from seed to seed.

DETAILED DESCRIPTION

The following is a detailed description of an embodiment of technology and methods enabling improved grain yield and modification of grain size, content and constituents. Such technology and methods may be used in association with any plants for which it is desired to produce grain. For ease of discussion and understanding, the following detailed description often refers to the invention for use with maize (also referred to as corn). It should be appreciated that the technology and methods may be used with any plants, and corn or other specifically named plants are discussed for illustration purposes only and are not intended to be limiting. The technology may be used in conjunction with any grain plant including those that are hybrids, non-hybrids, male fertile and male sterile.

Grain is produced for a number of purposes, including human consumption, animal consumption, industrial use, re-planting, and for research purposes. The primary goal of grain production is the harvesting of a high-yielding, high quality grain. Seed companies devote billions of dollars to research in the pursuit of developing better plant genetics in order to improve grain yields. Regardless of the end use of the grain, the production of grain is dependent on the appropriate male pollen fertilizing the appropriate female plant at the appropriate time.

The synchronization between the male pollen and the female receptivity is referred to herein as reproductive synchrony. Reproductive synchrony is easily achieved through self-pollination or pollination by neighboring plants of the same variety. However, reproductive synchrony is more difficult between different varieties which may mature at different times or as a result of different temperatures, as well as other environmental factors. A grain producer might have an interest in pollinating a crop with pollen from a variety that could impart specific characteristics to the resulting grain. Typically, this cannot be achieved unless the following circumstances exist: (1) the producer knows at the beginning of the growing season which variety they wish to pollinate with; (2) the varieties will be releasing pollen and receptive to pollen at the same time; and (3) the varieties are grown in close physical proximity to each other. So, for example, if a producer is experiencing a period of drought and would like to pollinate with a variety that shows strong grain yields even during drought periods, he will be unable to do so unless that is the variety that he has already chosen to plant and grow and it is already in his field, as well as releasing pollen at the appropriate time. This producer cannot typically pollinate a crop with pollen from a variety that might help overcome potential low grain yields due to drought if the variety is being grown elsewhere and has a different maturity period in comparison to his already planted variety. The present invention is able to overcome all three of these potential barriers to reproductive synchrony, thereby enabling a broader choice of pollen for the producer as well as the ability to make real-time production decisions.

Synchronous pollination within and between corn ears is particularly important in maize because it has been shown to improve kernel set, which is a critical factor in grain yields. Carcova (Carcova et al. (2000) *Crop Sci.* 40: 1056-1061) demonstrated that synchronous pollination of exposed silks on apical and sub-apical ears 5 days after silking showed an improvement in kernel number per plant.

Close synchrony between male and female flower anthesis, and a minimum pollen density per exposed silk are fundamental requirements for high levels of seed production and genetic purity. Previously collected and preserved pollen, or fresh pollen, can be applied to receptive silks over a period of seven to ten days, ensuring seed set under conditions of decreased pollen viability, silking delay relative to pollen shed, or poor 'nick' between male and female inbreds.

In the agronomic industry, "nick" is a term used in hybrid seed production that refers to the synchrony of both male and female flower types (i.e. the peak of pollen shed by the male aligned with the peak of silk emergence in the female) developing at the ideal time such that pollen grains will successfully pollinate, resulting in fertilization. For grain producers, the perfect "nick" occurs when 50% of the male population begins to shed pollen on the same day when 50% of the female population begins to exert silks.

A real-time production decision is a decision that is made during the pendency of the growth and maturation of the crop, rather than a decision that is made during the planning stage prior to the planting of the crop. Grain producers choose which grain variety to plant in any given production season based on characteristics that are optimal for their climate, land, growing conditions, and other factors. Once that decision has been made, and the crop has been planted, growers make real-time decisions during the growth of the crop, such as when to spray for weed control or treatment of disease or insect problems. These decisions occur as the crop grows in response to specific conditions and stresses that the crop is facing at any given time. Prior to this invention, however, grain producers have not been able choose pollen as a real-time production decision because the pollen used in grain production comes from the plants already growing in the field. Thus, the pollen choice is typically made at the time that the grain variety was chosen, prior to any planting, and without any knowledge of specific conditions that may occur later in the growing season affecting grain yield and viability.

The present invention is an improved method of grain production that includes collecting, storing, and delivering pollen from male plants to the female plants. Some methods of collecting pollen are known in the art. For example, U.S. Pat. No. 4,922,651 discloses an apparatus for effecting or improving pollination of plants.

In addition, some methods of pollen delivery, such as U.S. Pat. No. 4,922,651, are known in the art. In addition, various methods of pollen storage are known. For example, U.S. Pat. No. 5,596,838, covering a method and instrument for the preparation of pollen for cryogenic storage, teaches that pollen can be stored for periods of months and still remain viable. Although some methods of pollen delivery are known, these methods do not teach, suggest, or motivate the user to intentionally deliver pollen in such a way that allows the grower to take advantage of heterosis while also enabling real-time decision-making to improve yields based on current conditions. The present invention results in pollinations which occur prior to the active period in which the plant might be subject to self-pollination and/or be exposed to other undesirable pollination, or during the active period in which the plant is subject to self-pollination and/or exposed to other pollination, thereby increasing pollination efficiency. The present invention increases the heterosis effect, and allows for real-time production decisions. The invention does not require the use of male sterility or isolation, although one or both may be employed without departing from the scope of the invention.

As discussed above, the current invention is applicable to the common practice of planting seed that will germinate and become seed bearing plants that will bear the grain to eventually be sold to grain elevators or other customers, used as animal feed, or used in research programs. However, rather than relying exclusively upon self-pollination or pollination from neighboring plants as is the case with current practices, this invention provides an improved alternative by increasing successful self- and/or sib-pollination, and/or by modifying the level of cross-pollination through the intentional application of male pollen to female plants at a specific time. Use of the term "intentional" with regard to pollen application means the specific application of pollen in a way that does not include natural pollination by wind, insect activity or other naturally-occurring conditions. Intentionally applied pollen is pollen that has been applied to a plant as a result of a deliberate human activity or decision, and may be applied by hand or by other means. One example of intentional pollination is the "prescriptive" application of pollen, which is the use of pollen to solve a problem in order to address a specific need or condition in the field. The specific pollen to be used and the timing of the intentional application will depend upon the need or condition being addressed.

The acquisition of male pollen [sometimes "$pollen^M$"] required to make seeds that will mature into grain can be via a pollen bank. A pollen bank is a source of stored pollen that has been collected from one or more pollen sources and stored in such a way that the pollen retains its viability. The plants that have been used as the pollen source for such a pollen bank may have been grown and harvested in any conditions, including but not limited to, a field, a growth chamber, a greenhouse, a glasshouse, a shade house, a hoop house, a vertical farming facility or a hydroponic facility. Pollen from a pollen bank may have been sourced in different ways. For example, in one embodiment, fresh pollen can be harvested from males grown in a controlled environment in which the circadian rhythm is 2-8 hours ahead of naturally growing female plants in the field. This method will be further detailed below. In another embodiment, the pollen which is stored in the bank may be preserved pollen that was collected days, weeks, months or years prior to its eventual removal from the bank for pollinating purposes. Preserved pollen may have been preserved by any means that permits the pollen to retain viability, including but not limited to various forms of cooling or freezing including, but not limited to, chilling, cryopreservation, freeze drying, or storage in liquid nitrogen.

In one or more embodiments, the pollen may be harvested from an anther studio. The anther studio enables optimal growth conditions for male plant reproductive tissues for any species or variety of plant. The tissues (corn tassels for example) are cut from plants growing in standard outdoor conditions, such as in the field or those grown in controlled conditions, such as the greenhouse or a growth chamber. The tissues are preferably cut prior to the plant beginning to shed pollen and are placed into the anther studio. The tissue may then be cultured in a nutrient medium allowing for further growth. At least one of specialized lighting, temperature, and/or humidity may be cycled in the anther studio, allowing for continued growth of the tissue. Growth may be modulated to increase or slow the rate of growth and thus modulate the duration for availability of pollen. This enables the ability to have on demand pollen for pollinations that can be accomplished at any time of the day or night. This has utility for pollination enablement of several beneficial and valuable processes related to seed and grain production. It also provides concentrated sources of pollen for preservation purposes. Any pollen harvested from the anther studio and preserved could be utilized in the same manner as the freshly harvested pollen, but at a duration long after the fresh pollen, which has not been preserved, has died. (R. I. Greyson (1994) Maize inflorescence culture. p. 712-714. In: M. Freeling, V. Walbot (eds), The Maize Handbook; Springer-Verlag, New York: J. B. Schoper, R. J. Lamber, B. L. Vasilas, and M. E. Westgate (1987) *Plant factors controlling seed set in maize. The influence of silk pollen, and ear-learf water status and tassel heat treatment at pollination, Plant Phyiol.* 83: 121-125)

Mechanical delivery of the $pollen^M$ can occur as soon as females are receptive, which is always prior to the designated female pollen [sometimes $pollen^F$] becoming viable on any given day, thus enabling a successful cross pollination with all receptive females. In other words, the female component of the plant is open to receive pollen from a male before the male component of the same plant is actually ready to produce pollen. In corn, females are receptive to pollen when the silks are exposed to receive the pollen. The silks are receptive to pollen prior to emergence and remain receptive for many days after emerging from the husks. Moreover, in corn, two possibilities exist: pollen may be shed prior to silk emergence (protandry), or silk emergence may be prior to pollen shed (protogyny). In either case, the silks will be receptive to pollen before pollen is shed on a given day. This invention is applicable to both situations. Moreover, in some examples, the silks are receptive to pollen all day for about seven days. Accordingly, pollen may be intentionally applied any number of times, including but not limited to, once per day, twice per day, or in a continuous application. Alternatively, mechanical delivery of the $pollen^M$ can occur while females are viable and also during the period in which the designated female pollen [sometimes $pollen^F$] becomes viable on any given day, thus enabling both self-pollination with $pollen^F$ simultaneously with intentional pollination by $pollen^M$. Without the use of male sterility, in corn, for example, $pollen^F$ typically will begin to shed in the mid-morning hours, and continue to late morning or early afternoon, after which all $pollen^F$ either finds a viable female and germinates, enabling a successful self-pollination, or dies within four hours or less if it does not land on a viable female (Luna V. et al. (2001) Crop Sci. 41(5): 1551-1557). Thus, the female corn plant has a daily window of time during which male pollen can be delivered and during which $pollen^F$ is not shedding. This window will be repeated over several days. The current invention cross allows for the pollination of nearly all of the viable females during a window of time during which $pollen^F$ is not shedding or is not viable, or a combination of cross-pollination and self-pollination. The current invention has the capacity to cross pollinate nearly all of the viable females prior to $pollen^F$ becoming viable or after $pollen^F$ becomes viable, depending on the preference of the grain producer and the situation in the field.

Accordingly, one aspect of the invention is the timing of pollen delivery to female plants. In all crops, there is a daily cycle during the pollination window (the time during which the female is receptive to pollen and during which a successful pollination event can occur) in which females mature and grow relatively continuously, while males have a distinct cycle in which pollen becomes viable and sheds or is dehisced from the anthers beginning in mid-morning and ending in late morning or early afternoon. In some cases, $pollen^F$ can become viable prior to the females being fertile, but there will always be a first morning upon which viable females become fertile prior to viable $pollen^F$ beginning to shed on that day. Therefore, $pollen^F$ that may have shed the previous day has long since died and become inviable prior to females becoming viable the next morning. The early to mid-morning hours are therefore ideal for application of $pollen^M$ to fortuitously cross pollinate all viable females just prior to $pollen^F$ beginning to shed, although one may choose to apply pollen several days before $pollen^F$ beginning to shed or at several times of the day or in a continuous fashion even during the shed of pollen to increase the probability of successfully increasing heterosis effects, and maximizing the yield of grain. In one example, pollen may be delivered at 6:00 a.m. However, delivery of pollen may occur at any hour of the day, providing a great advantage over traditional methods.

By delivering pollen at the appropriate time and for the proper duration of a plant's fertility window, adequate pollination can be achieved. This invention enables for the first time effective grain production without solely relying upon self-pollination or pollination by neighboring plants which may, at the time of pollination, be an undesirable pollination option due to any number of biotic or abiotic stresses upon the crop. Undesirable biologically compatible sources can be referred to as pollen$^U$. The present invention allows for designated pollination such that when pollen$^U$ begins to shed, all viable target females have already been pollinated by the selected pollen source and the pollen$^U$ dies after a short period of time depending on species and environmental conditions (Luna V. et al. (2001) Crop Sci. 41(5): 1551-1557; Stanley, R. G. & Linskens, H. F. (1974) *Pollen: Biology, Biochemistry, Management*. Springer-Verlag. Heidelberg.; Shivanna, K. R. (2003) *Pollen Biology and Biotechnology*. Science Publishers, Inc.) without finding any viable target females, thus avoiding the pollination of females by an undesirable pollen source. This would be applicable to situations in which self pollen or neighboring plant pollen would be considered to be pollen$^U$. Different species of pollen have different lifespans, which may be further affected by environmental conditions (Dafni, A. & D. Firmage (2000) *Plant Systemics and Evolution* 222(1): 113-132). Higher humidity and lower temperatures may extend pollen longevity. For example, in rice (*Oryza sativa*), pollen longevity has been found to be as short as 4 minutes (Koga et al. (1971) *Cytologia* 36: 104-110) or up to 20 minutes for 50% of the pollen to die (Khatum, S. and T. J. Flowers (1995) *J. Exp. Bot.* 46: 151-154). In contrast, field grown radish (*Raphanus sativas*) pollen was shown to have a 5-day lifespan (Siddiqui, B. A. (1983) *Acta Bot. Ind.* 11: 150-154).

The capacity to deliver viable pollen on demand to effect timely pollinations of receptive silks addresses a number of limitations common to grain production on a field scale. Specifically, prescriptive use of the invention overcomes low levels of pollen production and eliminates problems caused by poor reproductive synchrony between male and female flowers.

Pollen$^M$ can be delivered in any number of ways, including, but not limited to, manual delivery, manual delivery with a small hand mechanical device for semi-automated dispersal, by field driven machinery containing pollen dispersal machinery or via fully automated dispersal by a self-propelled and/or human guided apparatus such as a drone that has a pollen dispersal device mounted to it, wherein the pollen dispersal is by automatic or semi-automatic means, including, but not limited to, positive pressure, negative pressure, mechanical or pneumatic means. Use of a drone would be especially novel and practical in this method. Small drones, which need not be regulated, can be used in the method, and can be guided using GPS coordinates to focus the pollen dispersal directly over the female plants. Using any of these methods, it has been estimated that about 140 grams (5 ounces) of pollen$^M$ fortuitously delivered for 3-4 consecutive days is enough to successfully cross pollinate one hectare (2.47 acres) of maize females. This estimate is based on literature that provides the number of maize pollen grains per mg, and estimating approximately 4-5 grains or pollen per silk, or fewer, for successful pollination (3-4 grains of pollen per silk is commonly accepted by those skilled in the art of pollination as the amount needed to ensure successful pollination (Westgate, M. E. et al. (2003) *Crop Sci.* 43: 934-942)). See, for example, Porter (1981) *Environ. Health Perspectives* 37: 53-59; Miller (1982) In *Maize for Biological Research*. W. F. Sheridan (ed.), pp. 279-293). The timing of pollen delivery, amount of pollen required, and number of days of pollen delivery can be adjusted as necessary for circumstances such as crop type and weather patterns, (i.e. crop height, crop density, rain frequency or amount, wind speed and direction, etc.). For example, the method can be adjusted for soybeans which have a longer pollination period than maize. Moreover, it is anticipated that the efficiency of these delivery methods will reduce the amount of pollen needed for successful pollination. It is estimated by the inventors that these more efficient methods may use 1/1000 of the amount of pollen currently produced for grain production. The inventors' research indicates that perfect corn kernel set requires about 3000 pollen grains per silk as shed normally in the field from maize tassels. Hand pollination studies and open field studies indicated about 3 to 4 pollen grains per silk ensure kernel set (M. E. Westgate et al. (2003) *Crop Sci.* 43: 934-942; M. Uribelarrea et al. (2002) *Crop Sci.* 42: 1910-1918). This results in a ratio of about 1/1000$^{th}$ of the amount of pollen currently required for grain production.

One skilled in the art can easily vary from the examples listed above as necessary. For example, in some situations, it may be advantageous to pollinate at night. In others, it may be advantageous to pollinate all day. In maize, pollination efficiency is improved when silk health is optimal and silk viability is at its maximum, which often coincides with conditions when the temperature is not as hot and when there is high moisture content in the air, meaning the silks are less likely to dry out quickly. Thus, a corn producer may choose timing of pollination to occur at the point when silk health and viability is optimal.

This invention can operate in any crop plant to either improve or enable grain production. It can operate in any environment including, but not limited to, ideal or target growing environments, off-season environments, or controlled environments (e.g. shade/glass/green/hoop houses, growth chambers, vertical farming facilities, hydroponic facilities, aeroponic facilities etc.). Pollen$^M$ can be applied as soon as females are viable and irrespective of pollen$^F$ or other undesired pollen viability. This invention can also be used to improve current grain production practices even when all conventional components are present, thus improving grain yields in challenging production situations.

In one embodiment, the invention may be used to solve or reduce the loss caused by drought. This is advantageous for all in the industry, including producers and crop insurers. Specifically, in a drought, plants become stressed. When a plant is stressed it often produces male components only. Accordingly, the pollen is there, but there are no females to receive it. Sometimes the plant will produce the female components later, but at that point the pollen is no longer available for pollination. By employing the method of the present invention, pollen may be delivered from a pollen storage bank or controlled environment to the stressed plants after the females are available for pollination, thus rescuing the plants to at least some degree to produce harvestable yields of grain.

Moreover, in another embodiment of the invention, real-time research or production decisions can be made with regard to the pollen intended to be used for pollination, such as the desire to produce grain with specific characteristics desired by the producer, including, but not limited to, increased oil production, decreased oil production, increased starch production, decreased starch production, improved drought resistance, improved resistance to flooding or other sources of excessive moisture, improved performance in high heat conditions, improved performance in low heat conditions, improved fungal resistance, improved insect resistance, increased yield, and improved pollination when the initial intended pollination is out of synchrony due to the male and female reproductive cycles being out of synchrony. All of these situations may be addressed by selecting pollen sources specifically optimized to maximize yields for any given condition for any given grain-producing crop of interest. Having a variety of pollen sources stored within a pollen storage bank enables these type of research or production decisions to be made just prior to pollen application. Specifically, the designated male pollen may be applied prior to, or during, self-pollination or exposure from the viable pollen from neighboring plants. The pollen storage bank from which the grower is sourcing their pollen may include male specific pollen sources optimal for application of pollen based on environmental conditions. Moreover, any pollen used in the present invention, including this embodiment, may include pollen from a single source or from multiple sources pooled together.

An example of a real time production decision includes the use of performance data in order to decide which male to use in a given hybrid cross or in grain production. For example, winter grain production is often practiced in the southern hemisphere outside of northern hemisphere growing seasons. Often, grain fields are planted in the southern hemisphere prior to complete performance data being collected in the northern hemisphere. Incomplete and/or delayed planting decisions are often made, resulting in poor decisions on the choice or volume of plants to be planted on the limited available land in the southern hemisphere. The current invention allows the producer to plant the female and then wait approximately 45 to 75 extra days in order to make a more informed decision about which male to use for pollinating female plants. This type of production decision would also apply for grain production in which a northern grain producer is waiting for more complete data from the southern hemisphere in order to decide which male to use.

As will be appreciated by one of skill in the art, the selection of the male pollen to be used in the practice of the invention is a significant factor in the potential benefit recognized by practicing the invention. Pollen vigor and viability are considerations, along with the various traits and characteristics that can be conferred by the pollen. There may be circumstances when using a pollen with lower vigor or viability is still a good choice because of the traits that it will confer upon the resulting grain. In such circumstances, when a pollen is known to have a lower vigor or viability, a more moderate resulting yield increase should be expected. Such decisions can be made by the grower based on the particular characteristics of the crop, the desired resulting grain, and prevailing conditions at the anticipated time of pollination with regard to environment and other biotic and/or abiotic pressures affecting the crop. Accordingly, the ability to select the pollen at the time of pollination is a further significant factor in the potential benefit recognized by practicing the invention. Table 1, below, outlines selected potential benefits of using the invention.

TABLE 1

Example Benefits of Pollen Selection

| Production Problem | Application of the Invention | Expected Benefit | Self Pollination, Cross Pollination or Both |
|---|---|---|---|
| Yield is limited due to self or sib pollination in grain production | Use of fresh or preserved pollen with a different genetic background applied to receptive silks on demand | Yield increase | Cross |
| Poor pollen production by males, not suitable for grain production on a field scale | Use of fresh or preserved pollen applied to receptive silks on demand thereby increasing pollination | Yield increases resulting from improved pollination | Both |
| Poor reproductive synchrony between male and female leading to low grain yield a | Use of fresh or preserved pollen applied to receptive silks on demand thereby increasing pollination | Increased grain yield per acre, decreased self pollination of females, decreased outcrossing from adventitious sources | Both |
| Low yield in top-cross production of high value grain | Use of fresh or preserved pollen applied to receptive silks on demand thereby increasing pollination | Increased yield of high value grain ensured by directing required male pollen to receptive silks, and potential for eliminating male pollinators from the grain field | Both |
| Organic or non-GMO contamination | Use of fresh or preserved pollen applied to receptive silks on demand thereby increasing purity | Increased purity of organic or non-GMO or specialty grain | Self pollination |
| Oil production modification desired | Use of fresh or preserved pollen containing traits for increased or decreases oil production applied to receptive silks thereby changing oil output | Increased yield and increased or decreased oil output in grain | Cross pollination |
| Starch production modification desired | Use of fresh or preserved pollen containing traits for increased or decreased oil production applied to receptive silks thereby changing starch output | Increased yield and increased or decreased starch output in grain | Cross pollination |
| Drought conditions prior to pollination | Use of fresh or preserved pollen to hit the nick wherein the pollen may or may not contain drought resistance traits | Rescue from drought. Yield increase | Cross pollination |
| Protein production modification desired | Use of fresh or preserved pollen containing traits for increased or decreased protein production applied to receptive silks thereby changing starch output | Increased yield and increased or decreased protein output in grain | Cross pollination |

TABLE 1-continued

Example Benefits of Pollen Selection

| Production Problem | Application of the Invention | Expected Benefit | Self Pollination, Cross Pollination or Both |
|---|---|---|---|
| Excessive heat or cold conditions | Use of fresh or preserved pollen containing heat or cold resistance traits | Rescue from extreme heat or cold. Yield increase | Cross pollination |
| Pressure from fungus | Use of fresh or preserved pollen containing fungal resistance traits | Rescue from fungal pressure. Yield increase | Cross Pollination |
| Pressure from insects | Use of fresh or preserved pollen containing insect resistance traits | Rescue from insect pressure. Yield increase | Cross Pollination |

As will be appreciated by one of skill in the art, the technology of this invention can be used to modify cross-pollination by increasing the level of cross-pollination (for example, in order to increase heterosis/xenia effect and thereby increase yield of a maize grain production field) but also can be used to reduce the level of cross-pollination and instead focus on self-pollination (for example, in an organic or non-GMO grain production scenario in order to increase successful self-pollination events and thereby reduce undesirable cross-pollination events). In such a case, the instant invention can be used to specifically avoid cross-pollination by enhancing self-pollination and thereby ensuring lower levels of cross contamination from undesirable pollen from GMO sources.

In addition, the current invention allows the producer to use a variety to pollinate the crop which would not normally be able to reach maturity or be a suitable pollinator in the producer's climate. Such a variety might have excellent characteristics that would make it a suitable cross-pollinator in order to maximize grain yield, but it cannot be grown in the producer's climate or will not be able to reach the stage at which it releases pollen in the producer's climate. The present invention overcomes this limitation and allows the producer a broader range of pollen types from which to select the ideal candidate for the particular crop and any particular stresses that may be present in the crop as the time for pollination approaches.

Another real time production decision made possible by the current invention is the decision of which pollen to use based on market and commodity price information. A grain producer would have approximately 45 to 75 extra days to watch the markets and decide which male to use for a specialty grain market, such as waxy corn versus food grade corn versus #2 yellow dent (commodity grain market).

Real time production decisions could also be made using environmental data. For example, a grain producer may have experienced a dry pre-flowering period and therefore may choose a male to pollinate the female that is known to be drought resistant. This decision will reduce seed abortion during drought stress, thus increasing yields in comparison to allowing the hybrid to self-pollinate to produce grain. A similar situation would exist for a producer experiencing high pressure for seed-feeding pests. A male could be selected that includes a gene for resistance to seed-feeding pests which will protect the developing seed and thus increase the hybrid seed yield relative to the yields that would have been obtained by using a male that was originally planned to be used before the pest problem arose, or that would have been planted in the more conventional block system. Environmental data used in real time production decisions could include, but is not limited to, abiotic conditions such as drought, nitrogen or other nutrient availability, humidity variation, and extreme temperature conditions; as well as biotic environmental conditions including, but not limited to, insect and nematode pest pressure, weed pressure, and disease pressure.

The following examples illustrate the present invention in more detail and are illustrative of how the invention described herein could be implemented in corn. The basic method could apply to any crop with crop specific modifications as appropriate. Examples 1 and 2 occurred in corn grain production fields in central Iowa during the summer of 2015.

Example 1

The invention described herein was practiced using a commercial hybrid (H1) as a female in one location in central Iowa. Blocks of 12 rows (width of 0.76 m (2.5 feet) per row for a total of 9.1 m (30 feet) in width) that were 13.7 m (45 feet) long of each hybrid were grown. One pollen donor inbred (P1) that was unrelated to H1 was grown at a distance of greater than 45.7 m (150 feet) away from the hybrid block. The pollen donor was a publicly available line from the USDA-ARS National Plant Germplasm System, and carried a gene for expression of anthocyanin in the endosperm of the kernel. When P1 is used as a male pollen source to pollinate, successful pollination of kernels is quickly obvious to the naked eye by observing the purple color of the mature kernels on an ear.

To practice the invention, water was sprayed on the tassels of the H1 grain production block (H1) at about 8:15 am to delay pollen shed from these female rows until about 8:45 am. After spraying the water on the female tassels, the invention was immediately practiced by coercing pollen$^M$ from the tassels of P1 and collecting the pollen in bags. The pollen$^M$ was then immediately applied to the H1 silks by hand using techniques well known in the art involving gentle tapping on the bag of pollen to release the pollen grains onto the silks. These pollinations occurred prior to the hybrids shedding any pollen. There were 13 pollinations made into the H1 grain production block by directing pollen onto the silks of the plants of H1 that were in the middle of the block. This imitated a case in which pollen may have been harvested by a nearby field of an unrelated corn hybrid, put into storage for a short period of time, and then brought out of storage in the early morning hours before pollen begins to shed from the hybrid grain production field being used as a female. Yellow kernels that are on these ears at harvest can be assumed to be mostly, if not all, self-pollinations from the H1 plants in the grain production block, while the purple kernels on these ears are the result of cross pollinations from the P1 pollen donor. It is important to note that manual direction of the pollen was very precise and measured, as there were only 2 purple kernels found on 6 adjacent ears that did not have P1 pollen directly applied to them (Table 2). These ears and resulting kernels served as controls to measure basal self-pollination percent in the block. Therefore, it can be inferred from this data that self-pollination frequency in the middle of this block of hybrids was very close to 100% under conventional methods of grain production. This experiment replicated what might be expected with the invention where pollen may have been harvested by a nearby field of an unrelated corn hybrid, put into storage for a short period of time, and then brought out of storage in the early morning hours before pollen begins to shed naturally from the hybrids being used as females The results in Table 2 show that the invention is very effective at increasing cross-pollination in this grain production field. Among the 13 ears upon which the invention was practiced, there were a total of 6,564 kernels, 2034 of which were purple, or 31% of the total. This is a huge increase in the frequency of cross-pollination of more than 38,000% (or 38-fold) compared to the 6 ears that served as a control. It is important to note that P1 and the other pollen donors mentioned in Example 2 below are non-elite inbreds that are more than 20 years old and were never bred for commodity grain yield. Further, based on the literature (Sari Gorla, (1975) *Theor. Appl. Genet.* 46:289-94), hybrid pollen, such as that from H1, is more fit and vigorous than inbred pollen. As a result, the P1 pollen had a competitive disadvantage in vigor and fitness compared to the H1 pollen. This further illustrates the effectiveness of the invention to increase cross-pollination.

TABLE 2

The effect of the invention on self- versus cross pollination percent in H1 using P1 male.

| Pollination type | Open-pollinated | | On-demand invention | |
|---|---|---|---|---|
| | # of kernels | % of total | # of kernels | % of total |
| Hybrid self pollination (yellow kernels) | 2452 | 100% | 4530 | 69% |
| Hybrid cross pollination (purple kernels) | 2 | 0% | 2034 | 31% |
| Total: | 2454 | | 6564 | |
| Increase in cross pollination frequency | | | 38021% | |

Example 2

The invention was practiced using 2 commercial hybrids (H1 and H2) as females in one location in central Iowa. Blocks of 12 rows (width of 0.76 m (2.5 feet) per row for a total of 9.1 m (30 feet) in width) that were 13.7 m (45 feet) long of each hybrid were grown. Three pollen donor inbreds (P1, P2, and P3) that were unrelated to these commercial hybrids were grown at a distance of greater than 45.7 m (150 feet) away from the hybrid blocks. The three pollen donors were publicly available lines from the USDA-ARS National Plant Germplasm System, and carried a gene for expression of anthocyanin in the endosperm of the kernel. When used as a male pollen source to pollinate, successful pollination of kernels is quickly obvious to the naked eye by observing the purple color of the mature kernels on an ear.

In the very beginning of the pollination window, the invention was practiced by coercing pollen$^M$ from the tassels of the pollen donor (P1, P2, and P3) males and collecting the pollen in the bags. The pollen$^M$ was then immediately directed to the H1 and H2 silks by hand using techniques well known in the art involving gentle tapping on the bag of pollen to release the pollen grains onto the silks. H1 was early maturing, as was P1, so P1 was used to pollinate onto H1 silks. It should be noted that a portion of the H1 ears in this experiment are comprised of 11 of the ears referred to in Example 1 above that fit the criteria to be included in this data set, and therefore were the result of the "spraying of water" to delay the males of H1 and were pollinations made prior to shedding of any H1 pollen. H2 was later maturing, as were P2 and P3. Therefore P2 and P3 were used to pollinate onto H2 silks. All pollinations onto H2 and the majority of the pollinations onto H1 occurred during the early onset of the pollination window in the morning, with the exception of the 11 pollinations onto H1 that occurred prior to the natural pollen window that were described in Example 1 above.

More than 75 hand pollinations were made into H1 and H2 by manually directing pollen onto the silks of the plants of H1 and H2 that were in the middle of the block during the early part of the natural pollination window. This method is a manifestation of the invention in which fresh pollen could be harvested in the early morning natural pollination window and immediately applied in a directed manner to a neighboring unrelated hybrid field. Further, this experiment imitated, although not exactly, a case where pollen may have been harvested by a nearby field of an unrelated corn hybrid, put into storage for a period of time, and then brought out of storage in the early morning hours before pollen begins to shed from the hybrids being used as females, and applied to those females. Pollinations were labelled with regard to which of the pollen donors was used for each pollinated ear. Yellow kernels that are on these ears at harvest can be assumed to be mostly, if not all, self-pollinations, while the purple kernels on these ears are the result of cross pollinations from the pollen donors. As noted in example 1 above, it can also be inferred that selfing in the middle of the blocks of hybrids in this experiment was also very near 100% when using conventional grain production methods.

Figure 2:
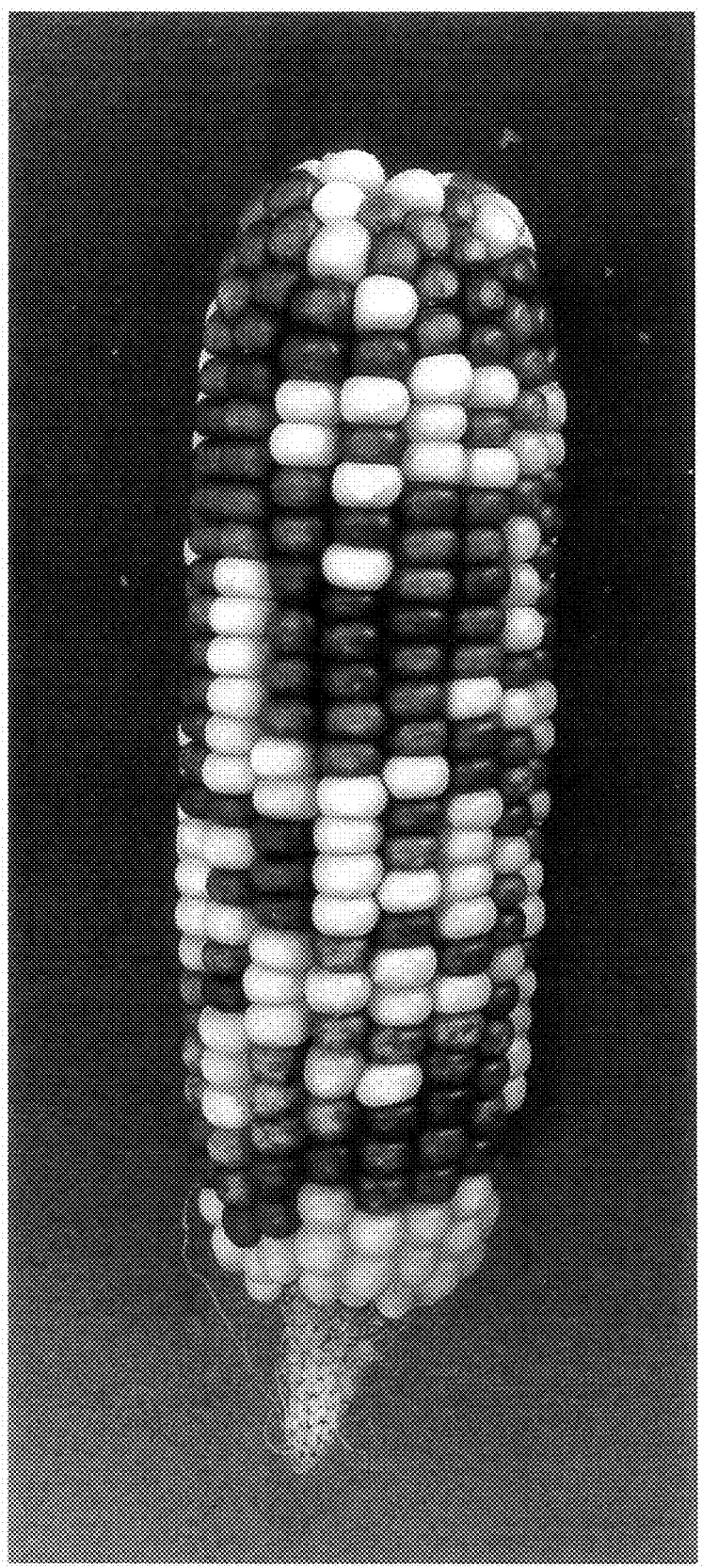
FIG. 2: This figure is a photograph of an ear of corn harvested from hybrid H2 and pollinated with pollen from pollen donor P2 as described in Example 2. The photograph is shown in black and white. The color version of the photograph shows the light colored kernels in yellow and the darker colored kernels in purple. This ear shows the successful cross-pollinations that occurred throughout the ear, and shows more cross-pollination than the ear in FIG. 1. The self-pollinations are the light kernels and the cross-pollinations are the dark kernels. This ear was useful for determining yield differences between the two pollination types.
Figure 3:
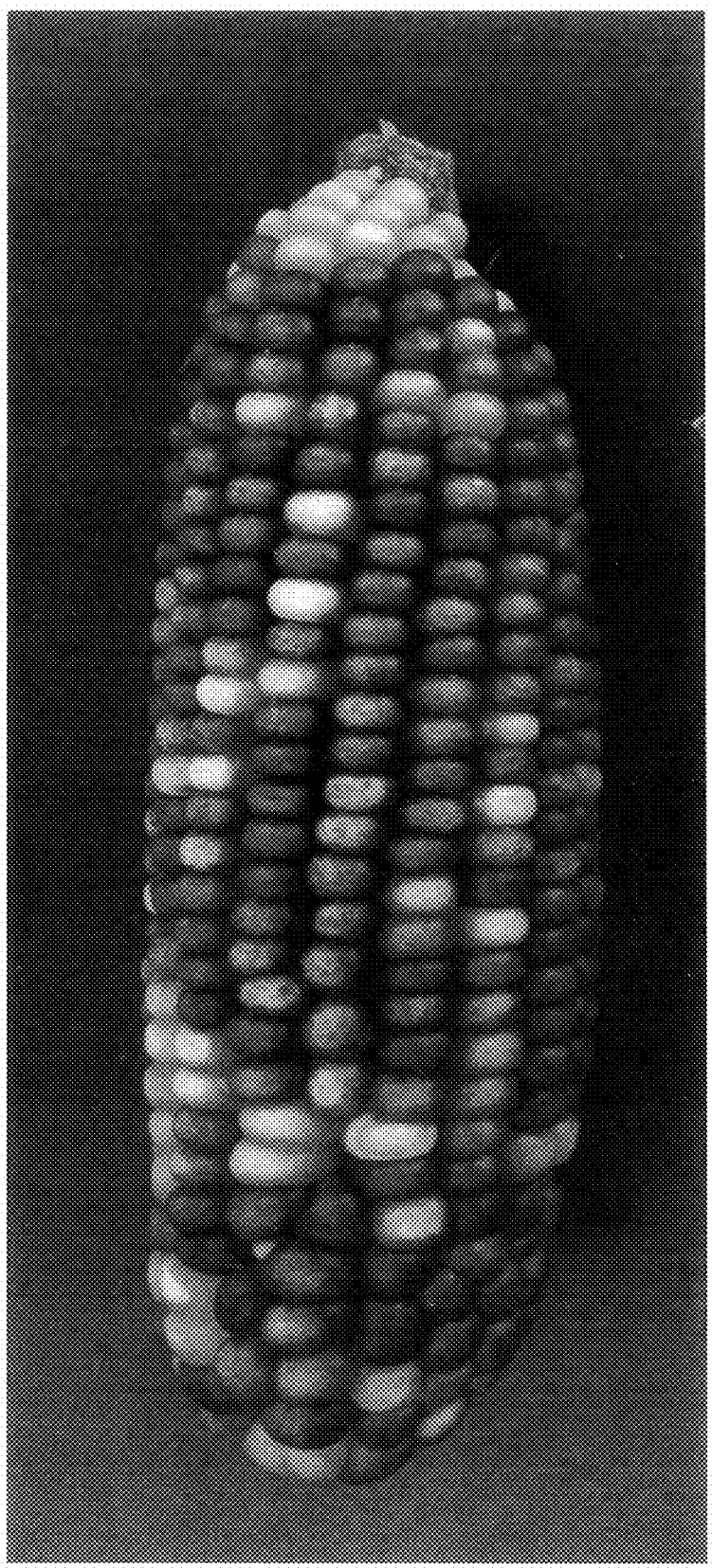
FIG. 3: This figure is a photograph of an ear of corn harvested from hybrid H2 and pollinated with pollen from pollen donor P2 as described in Example 2. The photograph is shown in black and white. The color version of the photograph shows the light colored kernels in yellow and the darker colored kernels in purple. This ear shows very high levels of cross-pollination (greater than 85%). The self-pollinations are the light kernels and the cross-pollinations are the dark kernels.

A portion of the harvested ears from the intentional pollinations had a high percent of cross pollinated kernels, often above 50%. These ears often had large blocks of purple kernels in one part of the ear, while the rest of the ear was yellow. This phenomenon can be seen in FIG. 3, which shows an ear with approximately 85% cross-pollination as shown by the high number of dark (purple) kernels. In other cases, there were ears that had a lower percent of purple kernels, often in the 10-30% range. Among these, there were a total of 49 ears that were a segregating mix of purple and yellow kernels, rather than solid blocks. Two sample ears are shown in FIGS. 1 and 2. These ears show a clear mix of dark (purple) and light (yellow) kernels. These ears were particularly diagnostic to illustrate the yield effect of self vs cross-pollination, whereas the ear shown in FIG. 3 was not diagnostic for illustrating yield because there were not enough self-pollinations to establish a sample size large enough for the comparison. The kernels on these ears developed in nearly identical environments, with the only difference among them being that they had different genetics from the male parent (self-pollination vs. cross). These kernels were harvested and separated into two groups for each ear: 100 yellow and 100 purple kernels from approximately the middle of the ear (sometimes when there were not enough purple kernels, a lower amount may have been used, with a minimum of 40 kernels of each type). Measurements were taken on these sets of kernels for each ear. Table 3a and 3b show the differences between yellow vs purple kernels from these ears for weight per kernel and test weight (weight per volume). The data from Tables 3a and 3b illustrate several points:

1. Practicing the invention resulted in higher yield for at least one measure (kernel weight or test weight), for the cross pollinated kernels than self-pollinated kernels in all three crosses (Tables 3a and 3b).

2. Practicing the invention may increase yield in different ways depending on the hybrid by pollen donor combination (Tables 3a and 3b). The first cross. H1 pollinated with P1, resulted in an 8.7% heavier kernel due to cross pollination, and 1.9% higher test weight. The second cross, H2 pollinated with P2, resulted in kernels that had 2.8% higher test weight but were not heavier per kernel. The third cross, H2 pollinated by P3, resulted in a 5.1% heavier kernel due to cross pollination, but test weight was not affected.

Tables 3a and 3b. The effect of self-pollination vs cross-pollination via practicing the invention on grain yield characteristics:

| Hybrid | Pollen donor | # of ears segregating for yellow and purple | yellow kernels g/kernel | purple kernels | grain weight increase due to cross pollination | P Value |
|---|---|---|---|---|---|---|
| H1 | P1 | 32 | 0.331 | 0.360 | 8.7% | <0.0001 |
| H2 | P2 | 11 | 0.309 | 0.313 | 1.3% (NS) | 0.2994 |
| H2 | P3 | 6 | 0.353 | 0.371 | 5.1% | 0.0002 |

| Hybrid | yellow kernels g/volume | purple kernels | Test weight increase due to cross pollination | P Value |
|---|---|---|---|---|
| H1 | 25.55 | 26.06 | 1.9% | <0.0001 |
| H2 | 26.52 | 27.27 | 2.8% | 0.0004 |
| H2 | 26.68 | 26.93 | 0.9% (NS) | 0.3574 |

Example 3

An example of the invention described herein is the common situation in commercial corn grain production where there are large fields (20.2-40.5 hectares (50-100 acres) per field or more) of different and unrelated hybrids, in many case from different commercial vendors. These fields will largely self-pollinate and therefore will incur lower yield than if they were cross pollinated with an unrelated pollen source. On average, a pure stand of corn will contain greater than 95% grain at harvest that is the result of self-pollination. Goggi et al. ((2006) *Field Crops Res.* 99: 147-157) showed outcrossing between adjacent grain fields was far less than this: 0.4% at 35 m, less than 0.05% at 100 m.). Many of these large fields of corn will be of different maturities and therefore flowering and shedding pollen at different times. In this example, the pollen from the earliest shedding field is collected and preserved/stored until the second unrelated hybrid field begins to flower, and then pollen from the first hybrid field is applied at an early morning hour (e.g. 5 am) to enhance cross pollination and minimize self-pollination in the second hybrid field. The application is conducted for two to three days in a row during the heaviest flowering days. The process is repeated by collecting, preserving, and storing the pollen from the second field and applying it to a third unrelated hybrid field when it begins to flower, and so on to a large number of fields until the flowering season ends. In this way, a significant portion of the corn grain in a region is the result of cross pollination rather than self-pollination, resulting in a yield increase in these fields of 5-10%. Further, this process does not have to be exactly sequential as described above. There would be adequate pollen from the first hybrid field (earliest to flower) to pollinate many fields (5 or more). In this way, the cross-pollination that occurs as a result of this invention could spread very quickly from one field to 5 in the second set of fields, to 25 in the third set, and so on. The result would be that cross-pollination is enabled in a large majority of corn fields in any given area.

Example 4

Another example of the invention described herein is similar to example 2 above in which pollen from unrelated hybrid fields that flower at approximately the same time is harvested as soon as the first tassels begin to shed in each field. A portion of the pollen from each field is immediately applied in a directed fashion to exposed silks in the other field, while the rest of the pollen is preserved/stored. The hybrid fields will flower for approximately 3-4 days, and the stored pollen is used in the following 2-3 successive days to pollinate in the early morning prior to natural pollen shed to enhance cross pollination. In this way cross-pollination is increased and therefore yields in both fields will be increased by 5-10%.

Example 5

In the specialty grain markets, it is very important that a field is allowed to entirely self-pollinate with very little cross pollination from other nearby corn. One example is "food grade" corn, in which there must be 99% selfing or more to meet the specifications (Strayer, D. (2002) *Preserved Systems: A reference handbook.* CRC Press.). In this example, the invention is utilized to decrease the amount of cross-pollination to enable a pure harvest of the target specialty grain that maintains the premium price with the end-user. In this case, pollen is harvested as soon as the first tassels begin to shed in the specialty grain field. A portion of the pollen is immediately intentionally applied in a directed fashion to exposed silks in the field. There is only a small percentage of silks that are exposed at this first stage of flowering. The rest of the harvested pollen is preserved/stored and is used in the following 2-3 successive days to pollinate in the early morning prior to natural pollen shed to enhance self-pollination and minimize cross-pollination. In this way, a specialty grain producer ensures a successful harvest and delivery of specialty grain that meets the end user specifications. This example could also be practiced in a less intense fashion by only applying the pollen to the outer edge, approximately 12.2 m (40 feet), of the field where most of the cross pollination is most likely to occur, and allowing the inner part of the field to pollinate naturally.

Example 6

This invention is applied to the corn grain industry in a way that allows for producer decisions to be made based on markets right up to the time of pollination (early to mid July) rather than making production decisions prior to planting, as is currently the case. Through the collection and preservation/storage of many different pollen sources, which are abundantly available in many different production situations globally, many different grain characteristics can be delivered to a hybrid field via the pollen selected to pollinate. A producer could watch the markets and decide among a specialty grain, such as high oil, or no 2 yellow dent commodity grain, and could place an order for the pollen that will deliver the grain desired. In this example, the hybrid that is planted is simply a female receiver for the pollen, and has generally desirable characteristics. The pollen contains the genes for the desired market and in this way a grain crop can be modified up until the time of pollination to match a market need. There are many other similar traits that apply in this example. For instance, if a drought is being encountered, a pollen source could be used that minimizes kernel abortion during grain fill. Alternatively, if the season has not been water limiting, a pollen source could be used that maximizes sink strength and grain yield.

For the examples given above (high oil vs no 2 yellow dent commodity grain) and many others, the characteristics could be achieved by utilizing naturally occurring, non-GMO pollen sources. For other traits, such as insect resistance in the grain, the desired characteristic could be achieved via a GMO source of pollen. Further, the current invention enables the delivery of GMO grain characteristics without the common concern of negative effects found in conventional GMO plants. In this way, this invention circumvents the massive hurdle that many beneficial GMOs have to get over to make it to market.

Example 7

A further example of the invention described herein is recovery of lost seed set under drought conditions that occur prior to or during the critical flowering period. Drought stress during this time is by far the greatest cause of lost grain production on an annual basis in the US. Under favorable conditions of adequate moisture and normal temperatures, there is close temporal synchrony between pollen shed from the male flowers in the tassels and emergence of the pollen receptive tissues of the female flowers (silks). Under drought conditions, however, three problems develop that disrupt the success of pollination. First, drought delays silk emergence relative to pollen shed. (Basset, P. & M. Westgate (1993) *Crop Sci.* 33: 279-282) That is, the Anthesis-Silking Interval (ASI) increases, which can completely prevent pollination of late emerging silks. Second, drought shortens the time emergent silks remain receptive to pollen. (Araus, J. L. et al. (2012) Front. Physiol. 3: 305) That is, their capacity to support pollen germination and pollen tube growth necessary or fertilization is diminished by several days. Third, high temperatures and low humidities that usually accompany a drought decrease pollen viability and longevity. (Schoper. J. B. et al. (1987) *Plant Physiol.* 83(1): 121-125). To apply the invention to this case, fresh pollen is harvested within the field, or a nearby field of an earlier maturing corn hybrid. The pollen is optionally stored for a period of time, and then applied directly to the female flowers as their silks emerge. This application overcomes all three of the referenced drought-based limitations on pollination and kernel set. The stored pollen can be applied on several successive days to enhance natural self/sib pollination. In situations where drought causes the ASI to increase to 4 days or more, application of the invention can increase yields by 25% or more.

Although various representative embodiments of this invention have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The invention claimed is:

1. A method of grain production, comprising:
   a. growing a designated female plant that includes both female and male components;
   b. intentionally cross-pollinating, on one or more days, said designated female plant with designated male plant pollen from a different genetic background when said male components are not shedding pollen on said one or more days;
   c. growing the designated female plant to maturity; and
   d. harvesting the grain produced by said designated female plant;
   wherein said male components are not male sterile at the time of cross-pollination and said female components are not covered to prevent undesirable pollination.

2. The method of claim 1 wherein said method results in one or more of the following:
   a. Increased grain yield, and
   b. Modified grain characteristics.

3. The method of claim 1 wherein the designated male plant pollen is comprised of one or more of the following:
   a. Fresh pollen, and
   b. Preserved pollen.

4. The method of claim 1 wherein said designated female plant is any one or more of: a corn plant, a soybean plant, a wheat plant, a rice plant, a sunflower plant, a canola plant, a sorghum plant, a barley plant, or a pearl millet plant.

5. The method of claim 1 wherein the intentional application of designated male plant pollen is conducted by any one or more of: mechanical means, pneumatic means, positive pressure means, negative pressure means, manual means, or combinations thereof.

6. The method of claim 1 wherein said designated male plant pollen is fresh pollen which has been harvested from one or more of a field, a growth chamber, a greenhouse, a glasshouse, a shade house, a hoop house, a vertical farming facility or a hydroponic facility.

7. The method of claim 1 wherein said designated male plant pollen is preserved pollen which has been previously collected and has been preserved by chilling, cooling, cryopreservation, freezing, freeze drying, or storage in liquid nitrogen.

8. The method of claim 1 wherein said designated male plant pollen is applied on more than one occasion to the same designated female plant.

9. The method of claim 8 wherein said designated male plant pollen is applied at the time which the female plant first becomes receptive to said pollen.

10. The method of claim 2 wherein the modified grain characteristics include one or more of grain size, grain content, or grain composition.

11. The method of claim 1 wherein said designated male plant pollen is obtained from sources optimal for application based on environmental conditions.

12. The method of claim 11 wherein said environmental conditions are abiotic conditions.

13. The method of claim 12 wherein said abiotic conditions include at least one of drought, humidity, temperature, nitrogen availability or nutrient availability.

14. The method of claim 11 wherein said environmental conditions are biotic conditions.

15. The method of claim 14 wherein said biotic conditions include at least one of insect pest pressure or disease pressure.

16. The method of claim 1 wherein said designated male plant pollen is obtained from sources optimal for application based on plant performance data.

17. The method of claim 1 wherein the designated male plant pollen influences the characteristics of the grain harvested from the female plant, wherein said influence impacts one or more of:
   i. grain oil content;
   ii. grain starch content;
   iii. grain protein content;
   iv. grain oil composition;
   v. grain starch composition; and
   vi. grain protein composition.

18. The method of claim 1 in which said designated male plant pollen is obtained from a single genetic source.

19. The method of claim 1 in which said designated male plant pollen is obtained from multiple genetic sources and is combined prior to application.

20. A method of preventing undesirable pollination in grain production, comprising:
   a. growing a designated female plant that includes female components that receive designated male plant pollen; and
   b. intentionally pollinating said designated female plant on one or more days with designated male plant pollen prior to said female plant being subjected to undesirable pollen on said one or more days;
   wherein said female plant is not male sterile at the time of cross-pollination and said female components are not isolated to prevent undesirable pollination; and
   wherein said undesirable pollen has the same genetic background as said designated female plant.

21. The method of claim 20 wherein the step of intentionally pollinating said designated female plant occurs prior to said designated female plant pollen becoming viable.

22. The method of claim 20 wherein the step of intentionally pollinating said designated female plant occurs at a time when said designated female parent plant pollen is not shedding.

23. The method of claim 20 wherein the step of intentionally pollinating said designated female plant occurs at a time when said designated female plant pollen is not shedding or viable.

24. The method of claim 20 wherein the step of intentionally pollinating said designated female parent plant occurs during the morning.

25. The method of claim 20 wherein the level of cross-pollination is modified compared to natural pollination.

* * * * *